United States Patent

Bernardin et al.

[11] 4,212,647
[45] Jul. 15, 1980

[54] WATER-INSOLUBLE AZO DYESTUFFS WHICH ARE DERIVATIVES OF 1-ARYL-3-TRIFLUOROMETHYL-5-PYRAZOLONES

[75] Inventors: Jacques A. N. Bernardin, Deuil La Barre; Jacques P. E. Pechmèze, Paris, both of France

[73] Assignee: Produits Chimiques Ugine Kuhlmann, Paris, France

[21] Appl. No.: 940,401

[22] Filed: Sep. 7, 1978

Related U.S. Application Data

[63] Continuation of Ser. No. 749,865, Dec. 13, 1976, abandoned.

[30] Foreign Application Priority Data

Dec. 17, 1975 [FR] France .................. 75 38615

[51] Int. Cl.² .............................. C09B 29/38
[52] U.S. Cl. ........................... 8/662; 8/584; 8/587; 260/163; 260/160
[58] Field of Search ............ 260/163, 160; 548/367; 8/41 C, 89, 41 R

[56] References Cited

U.S. PATENT DOCUMENTS 2,908,677 10/1959 Straley et al. ............. 260/163 X

OTHER PUBLICATIONS

Swarts, Bull. Sc. Acad. Roy. Belg., 1926, 12, pp. 692–721, at 720.
*Colour Index*, 3rd Ed., vol. 4, 1971, C.I. 12690–12750.
Lubs, *The Chemistry of Synthetic Dyes and Pigments*, Reinhold Publishing Corp., New York, 1955, pp. 670–671.

*Primary Examiner*—Arthur P. Demers
*Attorney, Agent, or Firm*—Beveridge, Degrandi, Kline & Lunsford

[57] ABSTRACT

Water-insoluble azo dyestuffs corresponding to the formula:

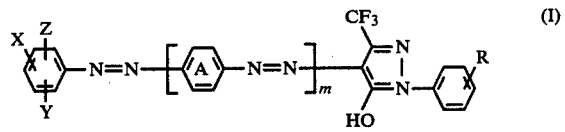

in which
- X represents halogen, cyano, nitro, alkyl, polyfluoroalkyl, polyfluoroalkoxy, alkylsulphonyl, sulphonamido, or sulphonamido substituted by one or two alkyl groups;
- Y and Z are the same or different and represent hydrogen, halogen, cyano, nitro, alkyl, alkoxy, polyfluoroalkyl, polyfluoroalkoxy, alkylsulphonyl, sulphonamido or sulphonamidosubstituted by one or two alkyl groups;
- R represents hydrogen, halogen, cyano, nitro, alkyl, alkoxy, polyfluoroalkyl, polyfluoroalkoxy, alkylsulphonyl, sulphonamido, or sulphonamido substituted by one or two alkyl groups;
- m is equal to 0 or 1;
- and the nucleus A may be substituted by one or more chlorine atoms or alkyl, alkoxy or acylamino groups.

These dyestuffs may be used for dyeing synthetic or artificial textile fibers, especially polyester fibers.

12 Claims, No Drawings

WATER-INSOLUBLE AZO DYESTUFFS WHICH ARE DERIVATIVES OF 1-ARYL-3-TRIFLUOROMETHYL-5-PYRAZOLONES

This is a continuation of application Ser. No. 749,865 filed Dec. 13, 1976 and now abandoned.

The present invention relates to new water-insoluble azo dyestuffs useful for dyeing artificial or synthetic textile fibers such as, for example, fibers based on cellulose acetate or polyesters.

The novel compounds of the present invention may be represented by the general formula:

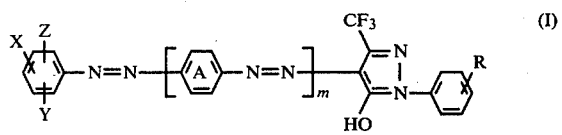

(I)

in which
- X represents halogen, cyano, nitro, alkyl, polyfluoroalkyl, polyfluoroalkoxy, alkylsulphonyl, sulphonamido or sulphonamido substituted by one or two alkyl groups;
- Y and Z are the same or different and represent hydrogen, halogen, cyano, nitro, alkyl, alkoxy, polyfluoroalkyl, polyfluoroalkoxy, alkylsulphonyl, sulphonamido or sulphonamido substituted by one or two alkyl groups;
- R represents hydrogen, halogen, cyano, nitro, alkyl, alkoxy, polyfluoroalkyl, polyfluoroalkoxy, alkylsulphonyl, sulphonamido or sulphonamido substituted by one or two alkyl groups;
- m is equal to 0 or 1,
- and the nucleus A may be substituted by one or more chlorine atoms or alkyl, alkoxy or acylamino groups.

In the definitions given above for X, Y, Z, R and for the possible substituents of the nucleus A, halogen is preferably chlorine or bromine; alkyl and alkoxy have preferably one or two carbon atoms, the alkyl and alkoxy chains of the polyfluoroalkyl, polyfluoroalkoxy and alkylsulphonyl groups have preferably 1 or 2 carbon atoms, and acylamino is preferably acetylamino. Specific examples of polyfluoroalkyl and polyfluoroalkoxy groups are trifluoromethyl, pentafluoroethyl and trifluoromethoxy groups. As will be seen in these examples the polyfluoro is usually perfluoro; i.e. complete substitution of the H atoms by fluorine.

While the present invention relates broadly to the dyestuffs of formula (I), it is more particularly directed to those dyestuffs wherein m is equal to 0 and R is hydrogen or nitro.

The azo compound of the formula:

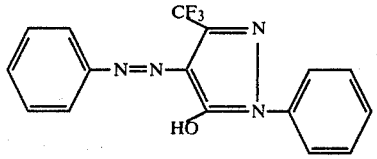

has been described by F. Swarts (Bull. Sc. Acad. Roy. Belg., 1926, 12, 720), but it has never been proposed for use as a coloring matter for dyeing textile fibers.

The compounds of formula I may be prepared in accordance with the invention by diazotising an amine of the formula:

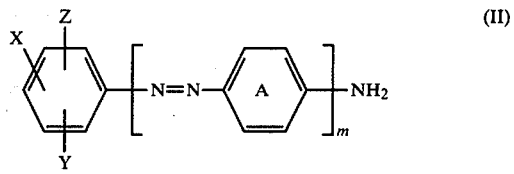

(II)

in which X, Y, Z, A and m have the same significance as in formula (I), then coupling the diazonium salt thus obtained with a 1-aryl-3-trifluoromethyl-5-pyrazolone of the formula:

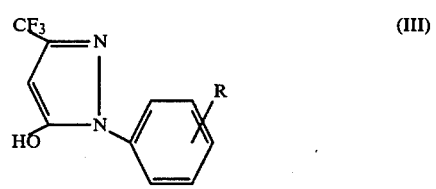

(III)

in which R has the same significance as in formula (I).

The amines of formula (II) are known products. In particular, those amines which contain a polyfluoroalkyl or polyfluoroalkoxy substituent have been described together with their processes of preparation in various publications. Representative publications includes Dickey et al, *Industrial and Engineering Chemistry*, Vol. 45, 1953, 1730 to 1740; Jones, *Journal of the American Chemical Society* 69, 1947, 2346; Yagupolsky et al, *Chemical Abstracts*, 51, 1957, 15,517; *Chemical Abstracts*, 55, 1961, 23,408; *Chemical Abstracts*, 70, 1969, 96,318; Sheppard, *Journal of Organic Chemistry*, 29, 1964, 1; *Journal of the American Chemical Society* 87, 1965, 2410 to 2420; McLoughlin and Thrower, *Tetrahedron*, 25, 1969, 5921 to 5940; and U.S. Pat. Nos. 3,058,973 and 3,281,426. Further, these amines are also described in French patent application No. 75 05410 filed in France on Feb. 21, 1975.

The coupling components of formula (III) are new products, with the exception of 1-phenyl-3-trifluoromethyl-5-pyrazolone. These coupling compounds may be prepared by condensation, in an acid medium, of ethyl trifluoroacetoacetate with a substitued phenylhydrazine of the formula:

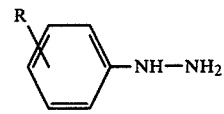

in which R has the same significance as in formula (I), according to a process similar to that described in the *Journal of Organic Chemistry*, 23, 1958, 119, for the preparation of 1-phenyl-3-trifluoromethyl-5-pyrazolone.

The dyeing of synthetic and artificial fibers by means of the dyestuffs of formula (I) is effected according to the conventional processes for dyeing those fibers with the usual plastosoluble dyestuffs.

In view of their tinctorial applications it is advantageous to put the dyestuffs of formula (I) in a finely divided form, for example, by grinding and dispersion with dispersing agents. Any suitable dispersing agent may be used such as, for example, the lignosulphonates. Accordingly, another aspect of the invention resides in dyestuff pastes containing the dyestuff of this invention in finely divided form dispersed in a dispersing agent that is inert with respect to the dyestuff and the textile fiber dyed therewith.

The dyestuffs of formula (I) have a good affinity for the synthetic and artificial fibers and this property is little affected by the conditions of the dyeing. For example, on polyester fibers, the affinity of the dyestuffs is practically the same whether the operation is carried out at 120°–130° C. without a vehicle or at 100° C. with a vehicle. The dyestuffs of formula (I) also show very high rates of saturation; that is the maximum amounts of dyestuff capable of being absorbed on the fibers under the usual conditions of dyeing.

When employed in the dyeing of synthetic and artificial fibers, the dyestuffs of formula (I) yield yellow to scarlet shades of considerable brilliance and good fastness to light. The dyeings obtained also have a good fastness to the wet tests. Furthermore, when they are mixed with blue dyestuffs, the dyestuff of formula (I) do not show the phenomenon of preferential degradation by light.

When compared with compounds having a methyl group on the pyrazolone ring instead of the trifluoromethyl group, the dyestuffs according to the invention show unexpectedly a better affinity for the fibers of polyesters and a better fastness to light.

The following examples in which the parts are parts by weight unless indicated otherwise, illustrate the invention.

EXAMPLE 1

12.8 parts of 4-chloroaniline were dissolved in 300 parts of normal hydrochloric acid. The solution was cooled to 0° C. and a solution of 7 parts of sodium nitrite in 100 parts of water was added while stirring, without exceeding a temperature of +5° C. The mixture was stirred for 30 minutes, then run into a solution of 22.8 parts of 1-phenyl-3-trifluoromethyl-5-pyrazolone and 30 parts of sodium acetate in 400 parts by volume of acetic acid.

When the coupling reaction was completed, the precipitated dyestuff was filtered off, washed with distilled water until the mineral salts were completely eliminated, and then dried in an oven at 50° C. The yield obtained was 36 parts of a dyestuff of the formula:

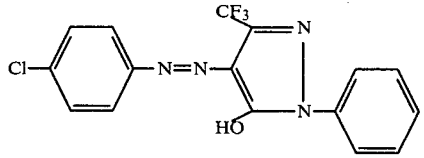

of which the elementary analysis was determined as follows:

|  | C% | H% | N% |
| --- | --- | --- | --- |
| Calculated for $C_{16}H_{10}ClF_3N_4O$ | 52.40 | 2.75 | 15.28 |
| Found | 52.48 | 2.68 | 15.35 |

15 parts of the dyestuff thus obtained were ground with 35 parts of the lignosulphonate known by the commercial trademark "Reax 80 C", 250 parts by volume of Ottawa sand and 125 parts of distilled water until a finess of the order of one micron was obtained. The dispersion was separated from the sand and dried in an oven at 50° C. The dyestuff dispersion obtained by this procedure dyes fibers of polyester a bright yellow shade which has an excellent fastness to light.

The 1-phenyl-3-trifluoromethyl-5-pyrazolone used as the coupling component may be obtained as follows:

A mixture of 184 parts of ethyl trifluoroacetoacetate, 120 parts of phenylhydrazine, 200 parts by volume of ethanol and 20 parts by volume of 22° Bé hydrochloric acid was heated under reflux, with stirring, for one hour, then 500 parts of water were added and the product was cooled in ice. The yellow precipitate obtained was filtered off, drained, washed, with a small portion of chilled toluene until decoloration took place. Thereafter it was dried in an oven (50° C.). 215 parts of 1-phenyl-3-trifluoromethyl-5-pyrazolone was obtained of which the melting point was 193° C.

Elementary analysis:

|  | C% | H% | N% | F% |
| --- | --- | --- | --- | --- |
| Calcuated for $C_{10}H_7F_3N_2O$ | 52.64 | 3.90 | 12.28 | 25.00 |
| Found | 52.76 | 3.31 | 12.33 | 25.15 |

EXAMPLE 2

13.8 parts of 3-nitroaniline was dissolved in 50 parts of water and 50 parts by volume of 22° Bé hydrochloric acid. The solution was cooled to 0° C. and a solution of 7 parts of sodium nitrite in 100 parts of water was added with stirring, without exceeding +5° C. The mixture was stirred for 30 minutes, then run into a solution of 27 parts of 1-(3'-nitro-phenyl)-3-trifluoromethyl-5-pyrazolone and 60 parts of sodium acetate in 400 parts by volume of acetic acid.

When the coupling reaction was completed, the precipitated dyestuff was filtered off, wahsed with distilled water until the mineral salts were completely eliminated, and then dried in an oven at 50° C. The yield obtained was 42 parts of a dyestuff of the formula:

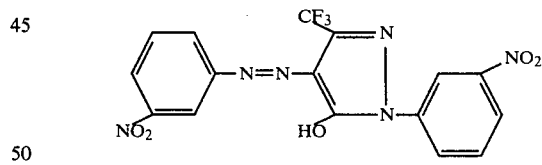

of which the elementary analysis was determined as follows:

|  | C% | H% | N% |
| --- | --- | --- | --- |
| Calculated for $C_{16}H_9F_3N_6O_5$ | 45.49 | 2.13 | 19.90 |
| Found | 45.50 | 2.07 | 19.71 |

After dispersing in accordance with the procedure shown in Example 1, this dyestuff dyed polyester fibers a green-yellow shade which demonstrated excellent general fastness.

The 1-(3'-nitrophenyl)-3-trifluoromethyl-5-pyrazolone used in this Example may be prepared according to the process described in Example 1, by initially replacing the 120 parts of phenylhydrazine by 153 parts of 3-nitro-phenylhydrazine. 258 parts of 1-(3'-nitrophenyl)-3-trifluoromethyl-5-pyrazolone were obtained with melting point 166° C.

Elementary analysis:

|  | C % | H % | N % | F % |
|---|---|---|---|---|
| Calculated for $C_{10}H_6F_3N_3O_3$ | 43.95 | 2.20 | 15.38 | 20.88 |
| Found | 43.99 | 2.17 | 15.14 | 20.87 |

EXAMPLES 3 to 43

Other examples of dyestuffs prepared according to the invention are listed in following Table I. The dyestuffs mentioned in this table are obtained by diazotisation of the amines of formula (II) shown in column 2 of the table and coupling the diazonium salts obtained with the coupling components of formula (III) shown in column 3 of the table.

In examples 3 to 16, and 32 to 37 the amines of formula (II) have been diazotised according to the procedure describec in Example 1 by initially replacing the 12.8 parts of 4-chloroaniline with an equimolecular quantity of the indicated amine of formula (II).

In Examples 17 to 31 and 38 to 43 the amines of formula (II) have been diazotised according to the procedure set forth in Example 2, by initially replacing the 13.8 parts of 3-nitroaniline by an equimolecular quantity of the indicated amine of formula (II).

TABLE I

| Ex. | Diazotizable amine of formula (II) | Substituent R of the compound of formula (III) | Formula of the dyestuff obtained | C % Cal. | C % Fd. | H % Cal. | H % Fd. | N % Cal. | N % Fd. | Shade on polyester |
|---|---|---|---|---|---|---|---|---|---|---|
| 3 | 2-chloroaniline | H | $C_{16}H_{10}ClF_3N_4O$ | 52.40 | 52.21 | 2.75 | 2.64 | 15.28 | 15.38 | yellow |
| 4 | p-aminoazobenzene | H | $C_{22}H_{15}F_3N_6O$ | 60.55 | 60.35 | 3.44 | 3.45 | 19.27 | 18.98 | orange |
| 5 | 4-trifluoromethoxyaniline | H | $C_{17}H_{10}F_6N_4O_2$ | 49.00 | 48.75 | 2.40 | 2.41 | 13.45 | 13.79 | yellow-green |
| 6 | 4-methylsulfonylaniline | H | $C_{17}H_{13}F_3N_4O_3S$ | 49.75 | 49.61 | 3.19 | 3.15 | 13.65 | 13.39 | yellow |
| 7 | 4-methylaniline | H | $C_{17}H_{13}F_3N_4O$ | 58.95 | 58.81 | 3.75 | 3.77 | 16.18 | 16.35 | " |
| 8 | 4-sulfonamidoaniline | H | $C_{16}H_{12}F_3N_5O_3S$ | 46.71 | 46.91 | 2.93 | 3.13 | 17.03 | 16.73 | " |
| 9 | 3-methylaniline | H | $C_{17}H_{13}F_3N_4O$ | 58.95 | 58.73 | 3.75 | 3.72 | 16.18 | 16.21 | " |
| 10 | 3-chloroaniline | H | $C_{16}H_{10}ClF_3N_4O$ | 52.40 | 52.09 | 2.75 | 2.67 | 15.28 | 15.26 | " |
| 11 | 2,5-dichloroaniline | H | $C_{16}H_9Cl_2F_3N_4O$ | 47.95 | 48.06 | 2.24 | 2.25 | 13.96 | 13.80 | " |
| 12 | 4-methylsulfonylaniline | 3-nitro | $C_{17}H_{12}F_3N_5O_5S$ | 44.83 | 44.61 | 2.63 | 2.59 | 15.38 | 15.03 | yellow-green |
| 13 | 4-chloroaniline | " | $C_{16}H_9ClF_3N_5O_3$ | 46.65 | 46.24 | 2.18 | 2.19 | 17.01 | 16.39 | " |
| 14 | 4-sulfonamidoaniline | " | $C_{16}H_{11}F_3N_6O_5S$ | 42.10 | 41.99 | 2.41 | 2.45 | 18.42 | 17.87 | " |
| 15 | 4-chloroaniline | 4-nitro | $C_{16}H_9ClF_3N_5O_3$ | 46.65 | 46.81 | 2.18 | 2.20 | 17.01 | 17.00 | yellow |
| 16 | 4-sulfonamidoaniline | " | $C_{16}H_{11}F_3N_6O_5S$ | 42.10 | 42.37 | 2.41 | 2.38 | 18.42 | 17.99 | " |
| 17 | 4-nitroaniline | H | $C_{16}H_{10}F_3N_5O_3$ | 50.92 | 51.17 | 2.65 | 2.85 | 18.56 | 18.57 | golden-yellow |
| 18 | 4-pentafluoroethylaniline | H | $C_{16}H_{10}F_8N_4O$ | 48.00 | 47.75 | 2.22 | 2.31 | 12.44 | 12.32 | yellow |
| 19 | 3-cyanoaniline | H | $C_{17}H_{10}F_3N_5O$ | 57.14 | 57.26 | 2.80 | 2.81 | 17.01 | 19.75 | " |
| 20 | 3-nitroaniline | H | $C_{16}H_{10}F_3N_5O_3$ | 50.92 | 51.24 | 2.65 | 2.66 | 18.56 | 18.43 | " |
| 21 | 3-trifluoromethylaniline | H | $C_{17}H_{10}F_6N_4O$ | 51.00 | 50.83 | 2.50 | 2.48 | 14.00 | 14.21 | yellow-green |
| 22 | 3-pentafluoroethylaniline | H | $C_{18}H_{10}F_6N_4O$ | 48.00 | 48.00 | 2.22 | 2.14 | 12.44 | 12.42 | " |
| 23 | 2-methyl-4-nitroaniline | H | $C_{17}H_{12}F_3N_5O_2$ | 52.17 | 52.52 | 3.07 | 3.15 | 17.90 | 17.72 | golden-yellow |
| 24 | 2-chloro-4-nitroaniline | H | $C_{16}H_9ClF_3N_5O_3$ | 46.66 | 47.15 | 2.19 | 2.48 | 17.01 | 16.39 | " |
| 25 | 2-cyano-4-chloroaniline | H | $C_{17}H_9ClF_3N_5O$ | 52.14 | 52.36 | 2.31 | 2.29 | 17.88 | 17.61 | yellow |
| 26 | 2-nitro-4-chloroaniline | H | $C_{16}H_9ClF_3N_5O_3$ | 46.66 | 46.95 | 2.18 | 2.20 | 17.01 | 16.73 | golden-yellow |
| 27 | 4-chloro-2-nitroaniline | 3-nitro | $C_{16}H_8ClF_3N_6O_5$ | 42.06 | 42.08 | 1.75 | 1.71 | 18.40 | 18.21 | yellow |
| 28 | " | 4-methyl | $C_{17}H_{11}ClF_3N_5O_3$ | 47.94 | 48.14 | 2.58 | 2.66 | 16.44 | 16.20 | golden-yellow |
| 29 | " | 4-chloro | $C_{16}H_8Cl_2F_3N_5O_3$ | 43.05 | 43.17 | 1.79 | 1.87 | 15.69 | 15.56 | " |
| 30 | " | 3-cyano | $C_{17}H_8ClF_3N_6O_3$ | 46.73 | 47.15 | 1.83 | 1.93 | 19.24 | 19.33 | yellow |
| 31 | " | 4-sulfonamido | $C_{16}H_{10}ClF_3N_6O_5S$ | 39.14 | 39.25 | 2.03 | 2.18 | 17.12 | 16.72 | " |
| 32 | p-aminoazobenzene | 4-chloro | $C_{22}H_{14}ClF_3N_6O$ | 56.11 | 56.08 | 2.97 | 3.01 | 17.88 | 17.95 | orange |
| 33 | 4-chloro-4-phenylazo-3-methylaniline | H | $C_{23}H_{16}ClF_3N_6O$ | 56.96 | 56.37 | 3.30 | 3.41 | 17.34 | 17.04 | orange |
| 34 | p-aminoazobenzene | 4-methyl | $C_{23}H_{17}F_3N_6O$ | 61.33 | 61.53 | 3.77 | 3.93 | 18.66 | 18.43 | orange |
| 35 | " | 3-nitro | $C_{22}H_{14}F_3N_7O_3$ | 54.89 | 54.80 | 2.91 | 3.04 | 20.37 | 20.74 | " |
| 36 | 4-chloroaniline | 3-trifluoromethyl | $C_{17}H_9ClF_6N_4O$ | 46.95 | 47.00 | 2.07 | 2.04 | 12.89 | 13.02 | yellow-green |
| 37 | " | 4-methylsulfonyl | $C_{17}H_{12}ClF_3N_4O_3S$ | 45.89 | 45.93 | 2.70 | 2.80 | 12.60 | 12.29 | " |
| 38 | 4-methyl-2-nitroaniline | H | $C_{17}H_{12}F_3N_5O_3$ | 52.17 | 52.21 | 3.07 | 3.25 | 17.90 | 17.80 | yellow |
| 39 | 4-methoxy-2-nitroaniline | H | $C_{17}H_{12}F_3N_5O_4$ | 50.12 | 50.16 | 2.95 | 3.11 | 17.20 | 17.22 | orange |
| 40 | " | 3-nitro | $C_{17}H_{11}F_3N_6O_6$ | 45.13 | 45.14 | 2.43 | 2.52 | 18.58 | 18.27 | " |
| 41 | " | 3-cyano | $C_{18}H_{11}F_3N_6O_4$ | 50.00 | 50.32 | 2.55 | 2.73 | 19.44 | 19.36 | " |
| 42 | 3-nitroaniline | 3-trifluoromethyl | $C_{17}H_9F_6N_5O_3$ | 45.84 | 45.80 | 2.02 | 1.95 | 15.73 | 15.73 | yellow-green |
| 43 | 4-chloro-2-nitroaniline | " | $C_{17}H_8ClF_6N_5O_3$ | 42.54 | 42.54 | 1.67 | 1.65 | 14.60 | 14.29 | yellow |

The coupling components 1-(4'-nitrophenyl)-3-trifluoromethyl-5-pyrazolone, 1-(4'-methylphenyl)-3-triflurormethyl-5-pyrazolone, 1-(4'-chlorophenyl)-3-trifluoromethyl-5-pyrazolone, 1-(3'-cyanophenyl)-3-trifluoromethyl-5-pyrazolone, 1-(4'-sulphonamidophenyl)-3-trifluoromethyl-5-pyrazolone, 1-(3'-trifluoromethylphenyl)-3-trifluoromethyl-5-pyrazolone, 1-(4'-methylsulfonylphenyl)-3-trifluoromethyl-5-pyrazolone identified in Table I were prepared according to the procedure described in Example 1 used for the preparation of 1-phenyl-3-trifluoromethyl-5-pyrazolone, by initially replacing the 120 parts of phenylhydrazine by an equimolecular quantity of the substituted phenylhydrazine which was used. Table II below lists the melting points and elementary analyses of these compounds.

TABLE II

| R in Coupling Component of formula (III) | Empirical Formula | Melting point °C. | Elementary Analysis | | | | | | | |
|---|---|---|---|---|---|---|---|---|---|---|
| | | | C % | | H % | | N % | | F % | |
| | | | Cal. | Fd. | Cal. | Fd. | Cal. | Fd. | Cal. | Fd. |
| 4-methyl | $C_{11}H_9F_3N_2O$ | 219 | 54.55 | 54.70 | 3.72 | 3.78 | 11.57 | 11.54 | 23.55 | 23.64 |
| 4-chloro | $C_{10}H_6F_3ClN_2O$ | 226 | 45.71 | 46.03 | 2.29 | 2.27 | 10.67 | 10.59 | 21.71 | 22.03 |
| 3-cyano | $C_{11}H_6F_3N_3O$ | 139 | 52.18 | 51.87 | 2.37 | 2.35 | 16.60 | 16.35 | 22.53 | 22.43 |
| 4-nitro | $C_{10}H_6F_3N_3O_3$ | 168 | 43.95 | 44.02 | 2.20 | 2.31 | 15.38 | 15.02 | 20.88 | 21.14 |
| 4-sulphonamido | $C_{10}H_8F_3N_3O_3S$ | 270 | 39.09 | 39.59 | 2.60 | 2.74 | 13.68 | 13.69 | 18.57 | 18.90 |
| 3-trifluoromethyl | $C_{11}H_6F_6N_2O$ | 210–211 | 44.59 | 44.75 | 2.02 | 2.01 | 9.46 | 9.61 | 38.51 | 38.29 |
| 4-methylsulphenyl | $C_{11}H_9F_3N_2O_3S$ | 260 | 43.14 | 43.32 | 2.94 | 2.93 | 9.15 | 9.17 | 18.62 | 18.90 |

EXAMPLE 44

26.2 parts of 2-bromo-4,6-dinitroaniline were dissolved in 100 parts by volume of concentrated sulphuric acid. The solution was cooled to 0° C. and a solution of acid nitrosyl sulphate obtained by mixing 8 parts of sodium nitrite with 100 parts by volume of concentrated sulphuric acid was added with stirring. After the introduction of the nitrosyl acid sulphate the reaction mixture was diluted with 400 parts by volume of orthophosphoric acid (d=1.7), while maintaining the temperature below 0° C. Stirring was continued for two hours at this temperature, then 13 parts of urea were added, and the mixture was stirred for a further 15 minutes and the acid solution then poured on 2000 parts of crushed ice.

The clear solution of the diazonium salt thus obtained was run while stirring into a solution of 22.8 parts of 1-phenyl-3-trifluoromethyl-5-pyrazolone in 400 parts by volume of glacial acetic acid. During the addition of the diazonium salt the mixture was maintained at pH 4–5 by simultaneous addition of sodium acetate.

When the coupling was finished, the precipitated dyestuff was filtered off, washed with distilled water until the mineral salts were completely eliminated and dried in an oven at 50° C. 42 parts of a dyestuff of the following formula were thus obtained:

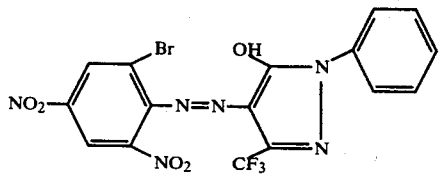

Of which the analysis is determined as follows:

| | C % | H % | N % |
|---|---|---|---|
| Calculated for $C_{16}H_8BrF_3N_6O_5$ | 38.35 | 1.61 | 16.77 |
| Found | 38.57 | 1.72 | 16.59 |

After dispersion as in Example 1, this dyestuff dyes polyester fibers a reddish-yellow shade which showed excellent general fastness.

EXAMPLE 45

Following the same procedure as in Example 44, but initially replacing the 26.2 parts of 2-bromo-4,6-dinitroaniline by an equimolecular quantity of 2-bromo-4-nitro-6-cyanoaniline, the dyestuff of the following formula is obtained.

of which the elementary analysis is as follows:

| | C % | H % | N % |
|---|---|---|---|
| Calculated for $C_{17}H_8BrF_3N_6O_3$ | 42.43 | 1.68 | 17.47 |
| Found | 42.86 | 1.67 | 17.48 |

This dyestuff dyes polyester based fibers a reddish-yellow shade.

EXAMPLE 46

Following the procedure described in example 44, but initially replacing the 26.2 parts of 2-bromo-4,6-dinitroaniline by an equimolecular quantity of 2,6-dichloro-4-nitroaniline, the dyestuff of the following formula is obtained:

of which the elementary analysis is as follows:

| | C % | H % | N % |
|---|---|---|---|
| Calculated for $C_{16}H_8Cl_2F_3N_5O_3$ | 43.05 | 1.79 | 15.70 |
| Found | 43.62 | 1.99 | 15.70 |

This dyestuff dyes polyester based fibers a yellow shade.

Further modifications of the invention will be apparent to those skilled in the art upon reading the foregoing specification.

We claim:

1. A dyestuff of the formula:

-continued wherein
X represents halogen, cyano, nitro, alkyl, polyfluoroalkyl, polyfluoroalkoxy, alkylsulphonyl or sulphonamido, or sulphonamido substituted by one or two alkyl, Y and Z are the same or different and represent hydrogen, halogen, cyano, nitro, alkyl, polyfluoroalkyl, polyfluoroalkoxy, alkylsulphonyl, sulphonamido or sulphonamido substituted by one or two alkyl, R represents hydrogen, halogen, cyano, nitro, alkyl, alkoxy, polyfluoroalkyl, polyfluoroalkoxy, alkylsulphonyl, sulphonamido or sulphonamido substituted by one or two alkyl;

m is equal to 0 or 1, and the nucleus A may be substituted by one or more atoms of chlorine or alkyl, alkoxy or acetylamino, halogen being chlorine or bromine and the alkyl, alkoxy, polyfluoroalkyl, polyfluoroalkoxy and alkylsulphonyl groups containing 1 or 2 carbon atoms.

2. A dyestuff according to claim 1 wherein m is equal to 0 and R represents hydrogen or nitro.

3. A dyestuff according to claim 6 represented by the structural formula:

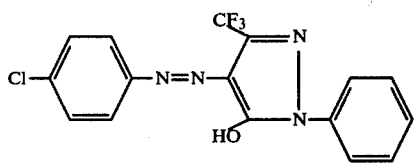

4. A dyestuff according to claim 2 represented by the structural formula:

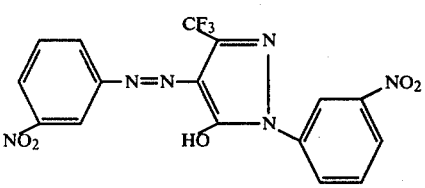

5. A dyestuff according to claim 2 represented by the structural formula:

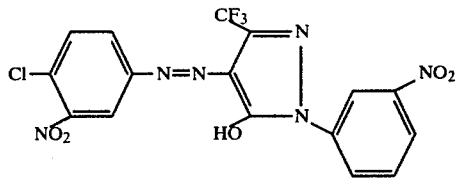

6. A dyestuff according to claim 2 represented by the structural formula:

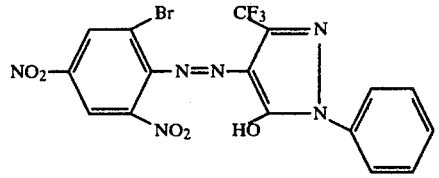

7. A dyestuff according to claim 1 wherein m is equal to 1.

8. A dyestuff represented by the structural formula:

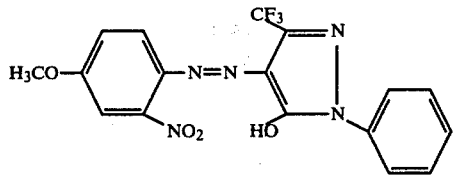

9. A dyestuff represented by the structural formula:

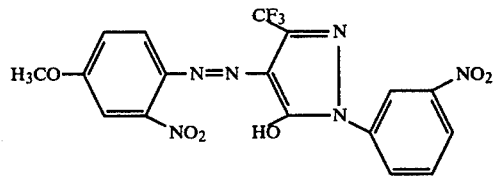

10. A dyestuff represented by the structural formula:

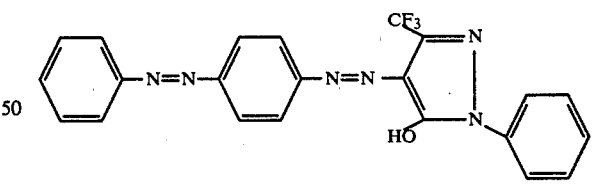

11. A textile fiber dyed with a dyestuff defined in claim 1.

12. A composition comprising a dyestuff according to claim 1 in finely divided form dispersed in a dispersing agent for the dyestuff.

* * * * *